US007862606B2

(12) United States Patent
Lootz et al.

(10) Patent No.: US 7,862,606 B2
(45) Date of Patent: Jan. 4, 2011

(54) STENTS MADE OF A MATERIAL WITH SHORT ELONGATION AT RUPTURE

(75) Inventors: Daniel Lootz, Rostock (DE); Karsten Koop, Rostock (DE); Frank Bakczewitz, Rostock (DE); Martin Kiekbusch, Stralsund (DE); Baerbel Becher, Rostock (DE)

(73) Assignee: Biotronik AG, Buelach (CH)

( * ) Notice: Subject to any disclaimer, the term of this patent is extended or adjusted under 35 U.S.C. 154(b) by 19 days.

(21) Appl. No.: 10/557,876

(22) PCT Filed: Apr. 15, 2004

(86) PCT No.: PCT/EP2004/003999
§ 371 (c)(1),
(2), (4) Date: Aug. 21, 2006

(87) PCT Pub. No.: WO2004/103215
PCT Pub. Date: Dec. 2, 2004

(65) Prior Publication Data
US 2007/0142899 A1 Jun. 21, 2007

(30) Foreign Application Priority Data
May 20, 2003 (DE) ............... 103 23 628

(51) Int. Cl.
*A61F 2/82* (2006.01)
(52) U.S. Cl. ..................... 623/1.16; 623/1.15
(58) Field of Classification Search ............... 623/1.15, 623/1.2, 1.16, 1.17
See application file for complete search history.

(56) References Cited

U.S. PATENT DOCUMENTS

| 5,733,303 | A | 3/1998 | Israel et al. | |
|---|---|---|---|---|
| 5,843,175 | A | 12/1998 | Frantzen | |
| 5,922,020 | A * | 7/1999 | Klein et al. | 623/1.15 |
| 6,066,169 | A | 5/2000 | McGuinness | |
| 6,217,608 | B1 * | 4/2001 | Penn et al. | 623/1.16 |
| 6,273,911 | B1 * | 8/2001 | Cox et al. | 623/1.15 |
| 2002/0004060 | A1 * | 1/2002 | Heublein et al. | 424/422 |
| 2002/0013619 | A1 * | 1/2002 | Shanley | 623/1.15 |
| 2002/0072793 | A1 | 6/2002 | Rolando et al. | |
| 2002/0095207 | A1 | 7/2002 | Moriuchi et al. | |
| 2002/0198593 | A1 * | 12/2002 | Gomez et al. | 623/1.16 |

FOREIGN PATENT DOCUMENTS

DE 689 17 501 T2 3/1995

(Continued)

*Primary Examiner*—David H Willse
*Assistant Examiner*—Megan Wolf
(74) *Attorney, Agent, or Firm*—Hahn Loeser & Parks, LLP; John J. Cunniff

(57) ABSTRACT

The invention relates to stents made of a material with an elongation at rupture of 30% or less and with a tubular base body which entirely or in parts comprises structural segments which are interconnected in longitudinal direction of the stents by means of transverse connectors and in which the structural segments comprise a zigzagging or undulating structure of a brace which is wrapped around the longitudinal axis of the stent. Due to the mechanical properties of the materials used, adaptation of the stent design is required. This is achieved in that in a turning region of the zigzagging or undulating structure the brace comprises a straight bending section aligned in circumferential direction.

16 Claims, 4 Drawing Sheets

FOREIGN PATENT DOCUMENTS

| | | |
|---|---|---|
| DE | 197 31 021 A1 | 1/1999 |
| DE | 199 45 049 A1 | 3/2001 |
| DE | 199 51 475 A1 | 5/2001 |
| DE | 100 44 043 A1 | 3/2002 |
| EP | 1 066 804 B1 | 7/2004 |
| WO | WO 99/40876 | 8/1999 |
| WO | WO 01/26584 A1 | 4/2001 |

* cited by examiner

STENTS MADE OF A MATERIAL WITH SHORT ELONGATION AT RUPTURE

BACKGROUND OF THE INVENTION

The invention relates to stents made of a material with an elongation at rupture of 30% or less and with a tubular base body which entirely or in parts comprises structural segments which are interconnected in the logitudinal direction of the stents by means of transverse connectors and in which stents the structural segments comprise a zigzagging or undulating structure of a brace which is wrapped around the longitudinal axis of the stent.

Coronary heart disease, in particular acute myocardial infarction, is one of the most frequent causes of death in Western Europe and North America. In more than 80% of cases, myocardial infarction is caused by thrombotic obstruction of a coronary artery as a result of rupture of atheromatous plaque in pre-existing stenosing atheromatosis. The following are decisive factors in the long-term prognosis after acute myocardial infarction:

- an effective and long-lasting reopening of the infarction artery;
- the duration of the thrombotic obstruction of the vessel;
- prevention of a major myocardial insufficiency and ventricular remodelling;
- gaining control over rhythmogenic complications.

The above-mentioned factors not only determine cardiovascular mortality but also the quality of life following the infarction.

Non-operative methods of stenosis treatment, in which among other things by means of balloon dilatation (percutaneous transluminal coronary angioplasty, PTCA) the restricted or obstructed blood vessel is opened up, have been established for more than twenty years. This procedure has proven reliable, in particular in the therapy relating to acute myocardial infarction. After the blood vessel has been expanded, in about a third of cases above-average proliferation occurs as a result of cell growth triggered by treatment, which proliferation finally leads to renewed angiostenosis (restenosis). The elasticity of the dilated blood vessel is a further cause of restenosis. After the balloon has been removed, the blood vessel contracts excessively so that the cross section of the vessel is reduced (obstruction, so-called negative remodelling). The latter effect can only be prevented, or at least impeded, by the placement of a stent.

In interventional therapy of stable angina pectoris with coronary heart disease, the introduction of stents has brought about a clear reduction in the rate of restenoses and thus to improved long-term results. This applies not only to primary stenosis but also to recidivation stenosis. An increase in the primary lumen gain is the major benefit of a stent implantation.

While the use of a stent can result in a more optimal vascular cross section, the presence of such a foreign object does however initiate a cascade of microbiological processes which can lead to a gradual closing up of the stent.

As a rule, a stent comprises a tubular base body with a circumferential wall made of braces and transverse connectors between which braces and connectors cells of various different shapes extend. A common feature of all typically used stents consists of the need, irrespective of the design of the stent, to allow expansion from a closed (non-expanded) state to an opened-up (expanded) state. In the non-expanded state, the stent is guided into the region of the lesion of the blood vessel. At the location of application the structure expands, either as a result of externally applied forces (e.g. by means of a balloon arranged in the interior of the stent) or as a result of the stent being designed so as to be self-expanding (e.g. by using a memory material).

A stent design must in particular meet the following requirements:

- in its expanded state, a stent must evenly support as large a surface of the wall of the blood vessel as possible;
- the design must support expansion of the stent in radial direction without allowing elongation in axial direction;
- in the non-expanded and expanded state and during the transition from the non-expanded to the expanded state, the individual braces and transverse connectors should, as far as possible, be arranged in a common radial circumferential plane, i.e. any projection of individual structural elements must be suppressed so as to prevent injury to the blood vessel;
- any failure of the material for the duration of the healing- and implantation period must be avoided.

Modern stent designs take account of these requirements with the use of typically employed stent materials.

Initially, stents were predominantly made from surgical steel, e.g. 316L. Over time it became clear, however, that while the materials used were biocompatible, in the medium to long term some of them encouraged thrombosis formation while others encouraged adhesion of biomolecules to their surfaces. Stents made from a biodegradable material provide a starting point to solving these problems. The term "biodegradation" relates to hydrolytic, enzymatic and other metabolic decomposition processes in the living organism which lead to gradual decomposition at least of large parts of the implant. For example, a multitude of plastic materials have been proposed as stent materials, which, while providing good biocompatibility and good degradation behaviour, due to their mechanical properties have at best been limited in their use for medical applications.

To overcome this disadvantage, the use of special biodegradable metal alloys has been envisaged, as described in particular in U.S. Pat. App. Pub. No. 2002/0004060 and DE 199 45 049 whose disclosure is herewith fully incorporated in this patent specification. The metal alloys comprise special iron alloys, tungsten alloys and magnesium alloys. However, these favoured materials are at least partly associated with a disadvantage in that their elongation at rupture is 30% or less so that all typically applied stent designs are thus excluded. For example, material 316 L has an elongation at rupture of 40-50%, determined on a tubular tensile test sample with a diameter of 1.6 mm and a wall thickness of 0.1 mm, at a sample length of 60 mm and a measuring length of 22 mm. A typical biodegradable magnesium alloy has an elongation at rupture of 14%, determined on a tubular tensile test sample with a diameter of 1.6 mm and a wall thickness of 0.2 mm, at a sample length of 50 mm and a measuring length of 30 mm.

In this context the term "rupture" refers to separation, caused by overloading, of the binding between atomic components of a material along a surface of fracture which extends across the entire width of the material sample. At the time of rupture, the tensions built up in the material as a result of external or internal forces exceed the material-specific stress at failure and thus exceed the binding forces that are effective in the surface of the fracture. The resistance to fracture states the force needed for a material sample to be loadable to fracture. Fractures without deformation or with little deformation can be compensated for without any problems with the use of the above-mentioned metal alloys. In contrast to this, deformation fractures such as transverse ruptures and torsion fractures are unavoidable with conventional stent designs because the elongation at rupture of the material is insufficient.

The term "elongation at rupture" refers to the remaining extension after a tensile test up to rupture, i.e. the difference in the length between the original sample and that of the fractured sample.

It is an aspect of the present invention to provide a stent design which is suitable for materials with an elongation at rupture of less than 30%.

SUMMARY OF THE INVENTION

The stent according to the invention comprises a material with an elongation at rupture of 30% or less and a tubular base body which entirely or in parts comprises structural segments. The structural segments are interconnected in longitudinal direction by way of transverse connectors and comprise a zigzagging or undulating structure made of a brace which is wrapped around the longitudinal axis of the stent. The stent is characterised in that the brace in a turning region of the zigzagging or undulating structure comprises a straight bending section that extends in circumferential direction. The bending sections according to the invention are integrated in the stent design such that when the stent expands from a non-expanded to an expanded state they are subjected to a tension moment and a bending moment. The alignment and shape, according to the invention, of the bending sections only relates to their non-expanded state, i.e. after expansion the bending sections normally have a different alignment and shape. During expansion, the straight alignment results in even tension distribution and expansion distribution. Only almost-straight bending sections are not optimal in this respect and only similar, approximately even, tension distribution and expansion distribution can be achieved. In the case of deformation of the structure, these straight bending sections are predominantly exposed to a bending moment. Due to the constant lever arm or the constant moment along the entire straight bending section, expansion is distributed evenly on this bending section. Local tension concentrations and expansion concentrations are largely prevented, and this measure takes account of the short elongation at rupture (<30%).

The limb sections are kept short enough that in the circumferential direction, they rise as the stent expands. This enforces geometrically even widening of the stent. This means that with increased widening, the length of the lever arm of the loops shortens considerably and thus significantly more force is required to open them. Since the reaction forces are constant for each segment across the circumference, therefore at first only other cells open up whose limb sections are less steeply inclined. The strengthening of the material is so low that it alone would not be adequate to ensure even opening-up of the structure in a conventional stent design. Moreover, raising of the limb section minimizes the recoil which is usually substantial due to the low e-module, because in this position the spring-back angle of the stent has only little influence on the spring-back travel. There is also a favourable influence on collapse pressure because the torsional load of the brace clearly diminishes as said brace is raised.

In an advantageous improvement of the stent design according to the invention, stop elements are arranged in the turning region of the zigzagging or undulating structure. They are designed such that deformations in the zigzagging or undulating structure, which deformations occur as a result of expansion from the non-expanded to the expanded state of the stent, are prevented in the region of the straight bending sections, and are reinforced in the region of the limbs. This is, in particular, achieved in that the stop elements are made from two webs, one end of which is affixed to the zigzagging or undulating structure. The free ends of the two webs are aligned with each other and are arranged such that during expansion of the stent they move towards each other until they rest against each other. From this point in time onward deformation in the straight sections is limited and transferred to the other deformation zones of the stent. This measure also leads to optimum distribution of expansion in the structure.

According to a further preferred embodiment of the stent design, the ratio of the length of a straight bending section of the brace to its width is 1:2 to 1:6, preferably 1:2 to 1:3. The width and length of the bending sections must be differentiated from their thickness, i.e. their expansion in radial direction. It has been shown that the above-mentioned specifications can particularly reliably prevent rupture of the material.

Furthermore, it is preferred if the stent comprises double-s-shaped limb sections. With this shape, the previously mentioned favourable characteristics on recoil behaviour and collapse pressure can be supported. Furthermore, it is advantageous if the limb sections are optimised with a view to the stress ratios that occur during expansion. In this respect, reference is made to U.S. Pat. Pub. Nos. 2002/0095140 and 2002/0049487, the disclosures of which are herewith fully incorporated into the present patent specification.

Furthermore, the material used for the stents preferably has an elongation at rupture of 5-30%, in particular 10-30%, particularly preferably 10-25%, particularly preferably 10-20%, particularly preferably 10-15%. In the diminished preferential ranges, the use of the stent design in comparison to alternative constructions has been shown to be particularly suitable.

Furthermore, it is preferred if the structural segments in longitudinal direction of the stent are arranged such that the zigzagging or undulating structures of at least two adjacent structural segments are in phase. In this way, a particularly even support structure in the expanded state is achieved and any change in length can be minimized.

Furthermore, the material is preferably a biodegradable metal alloy, in particular a tungsten alloy, magnesium alloy or iron alloy.

Moreover, it is advantageous that the transverse connectors are aligned parallel to the longitudinal direction of the stent. Such an arrangement supports even expansion of the structure during the expansion phase. In order to enhance the bending flexibility, it is furthermore advantageous if the transverse connectors that extend parallel to the longitudinal axis of the stent are of S-, V-, W- or some other multisinusoidal shape.

In principle, a starting point of the transverse connectors can be selected freely along the circumferential zigzagging or undulating structure. However, it has been shown to be advantageous if one point of contact of the transverse connectors is situated in the region of the straight bending sections, in particular in the middle of said bending sections. This measure, too, improves the expansion behaviour and helps achieve a more even support structure.

The alignment of the straight bending sections according to the invention is to be in circumferential direction of the stent, wherein slight deviations from the specified directions are tolerable without causing significant impairment in expansion behaviour. The deviation is preferably <25°, in particular <20°, particularly preferably <10°. In other words, a deviation in the alignment of the straight bending sections in circumferential direction of the stent is at most 25°, in particular at most 20°, particularly preferred at most 10°.

BRIEF DESCRIPTION OF THE SEVERAL VIEWS OF THE DRAWINGS

Below, the invention is explained in more detail by means of exemplary embodiments with reference to the associated drawings. The following are shown.

DETAILED DESCRIPTION OF THE INVENTION

The stents described below are formed from a biodegradable metal alloy. Metal alloys suitable for this purpose are described in U.S. Pat. Pub. No. 2002/0004060 and DE 199 45 049 whose disclosures are expressly incorporated by reference in these patent specifications. In particular, at least some of the magnesium alloys described therein with a composition of 50-98% magnesium, 0-40% lithium, 0-5% iron and less than 5% other metals, as well as at least some of the iron alloys described therein with a composition of 88-99% iron, 0.5-7% chromium and 0.5-3.5% nickel as well as less than 5% of other metals have an elongation at rupture of 30% or less.

Due to the mechanical characteristics of the above-mentioned materials, in particular their short elongation at rupture, a matched design is required. This will be explained in more detail below in the examples of FIGS. 1 and 2.

Embodiment 1

Figure 1:
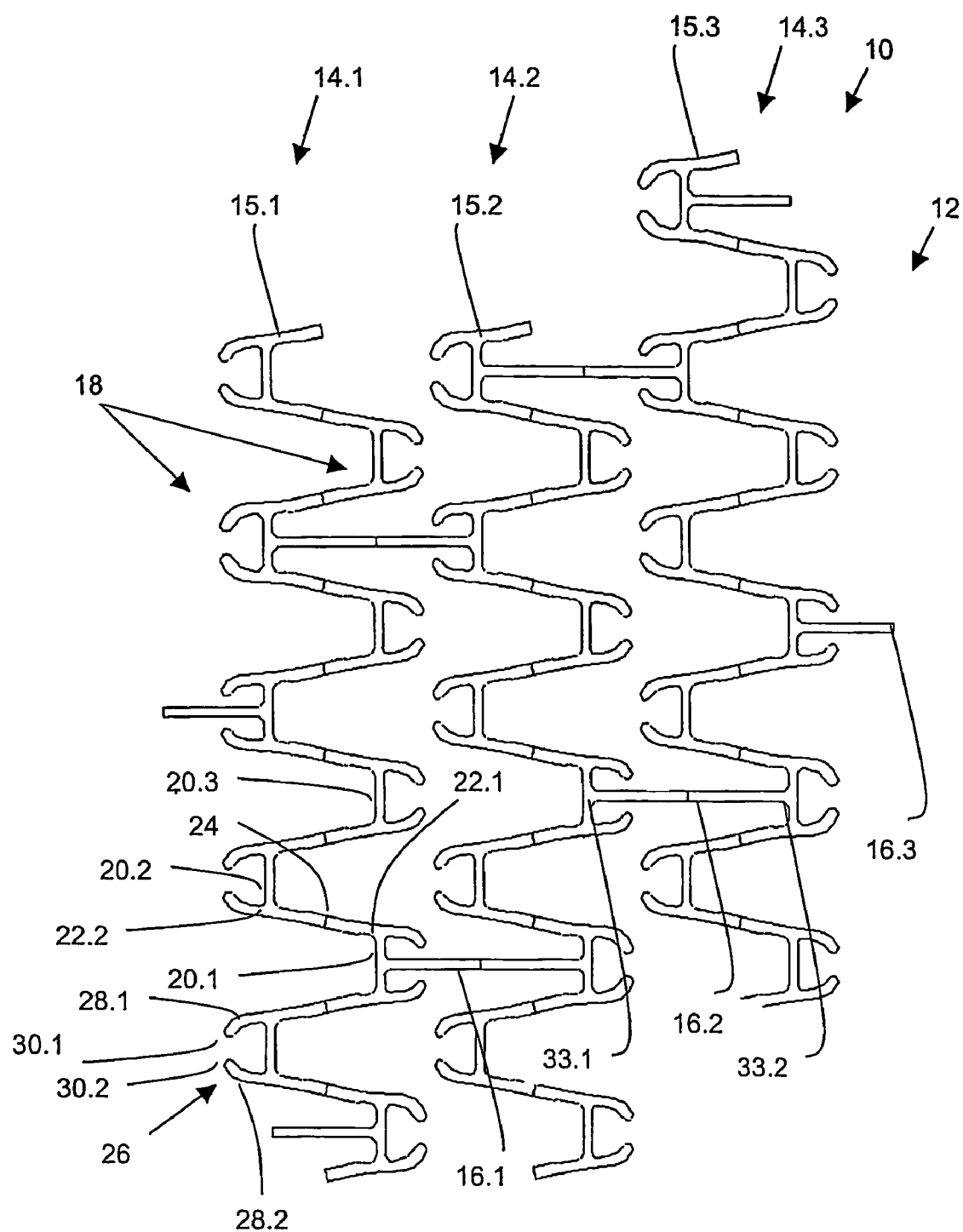
FIG. 1 is a diagrammatic section view of a stent design according to the invention according to a first variant.

FIG. 1 diagrammatically shows a section view of a stent 10, namely in a top view of the windings of its tubular circumferential wall 12. A base body of the stent 10 is composed entirely or in part of a multitude of structural segments 14.1, 14.2, 14.3. The individual structural segments 14.1, 14.2, 14.3 are interconnected by way of transverse connectors 16.1, 16.2, 16.3 aligned in longitudinal direction of the stent 10. The design of the transverse connectors 16.1, 16.2, 16.3 is shown only by way of an example.

In order to enhance the bending flexibility, variants with S-, V-,W -or some other multisinusoidal shape can also be used.

The structural segments 14.1, 14.2 and 14.3 of FIG. 1 comprise a zigzagging or undulating structure made from a brace 15.1, 15.2, 15.3 that extends circumferentially along the longitudinal axis of the stent 10. As shown in the illustration, in a turning region 18 of the zigzagging or undulating structure, i.e. in the peaks of the individual meanders, the braces 15.1, 15.2 and 15.3 comprise straight bending sections 20.1, 20.2, 20.3 extending in circumferential direction of the stent 10. The straight bending sections 20.1, 20.2 are interconnected by way of joining points 22.1, 22.2 and a limb section 24. In this specific case the length of a straight bending section 20.2 of the brace 15.1 in relation to its width 24 is approximately 1 to 3.5, wherein the length is measured from the geometric centres of the joining points 22.1, 22.2.

The transverse connectors 16.1, 16.2, 16.3 are aligned parallel to the longitudinal direction of the stent 10; they start at the points of contact 33.1, 33.2 approximately in the middle of each sixth straight bending section. Of course other points of contact and sequences are also imaginable. As shown in the illustration, the braces 15.1, 15.2, 15.3 extend in longitudinal direction of the stent 10 in phase, i.e. the turning regions 18 of the individual structural segments 14.1, 14.2, 14.3 share a common alignment.

Furthermore, the zigzagging or undulating structure comprises stop elements 26, which are designed in such a way that deformations of said zigzagging or undulating structure, which deformations occur as a result of expansion of the stent from the non-expanded to the expanded state, in the region of the straight bending sections 20.1, 20.2, 20.3, are reduced and in the region of the limb sections 24 is increased. In the present case the stop elements 26 are formed by two webs 28.1, 28.2 whose one end is connected to the zigzagging or undulating structure, for example in the illustration at the joining points 22.4 and 22.5. At their free ends 30.1, 30.2 the webs 28.1, 28.2 are curved such that they are aligned with each other. During expansion of the stent 10 the free ends 30.1, 30.2 move towards each other until they rest against each other. From this moment onward, further deformation of the straight bending sections 20.1, 20.2, 20.3 is prevented or at least made more difficult. Consequently, displacement of the deformation into the deformation zones of the stent 10, which deformation zones are formed by the limb sections 24, takes place.

Embodiment 2

Figure 2:
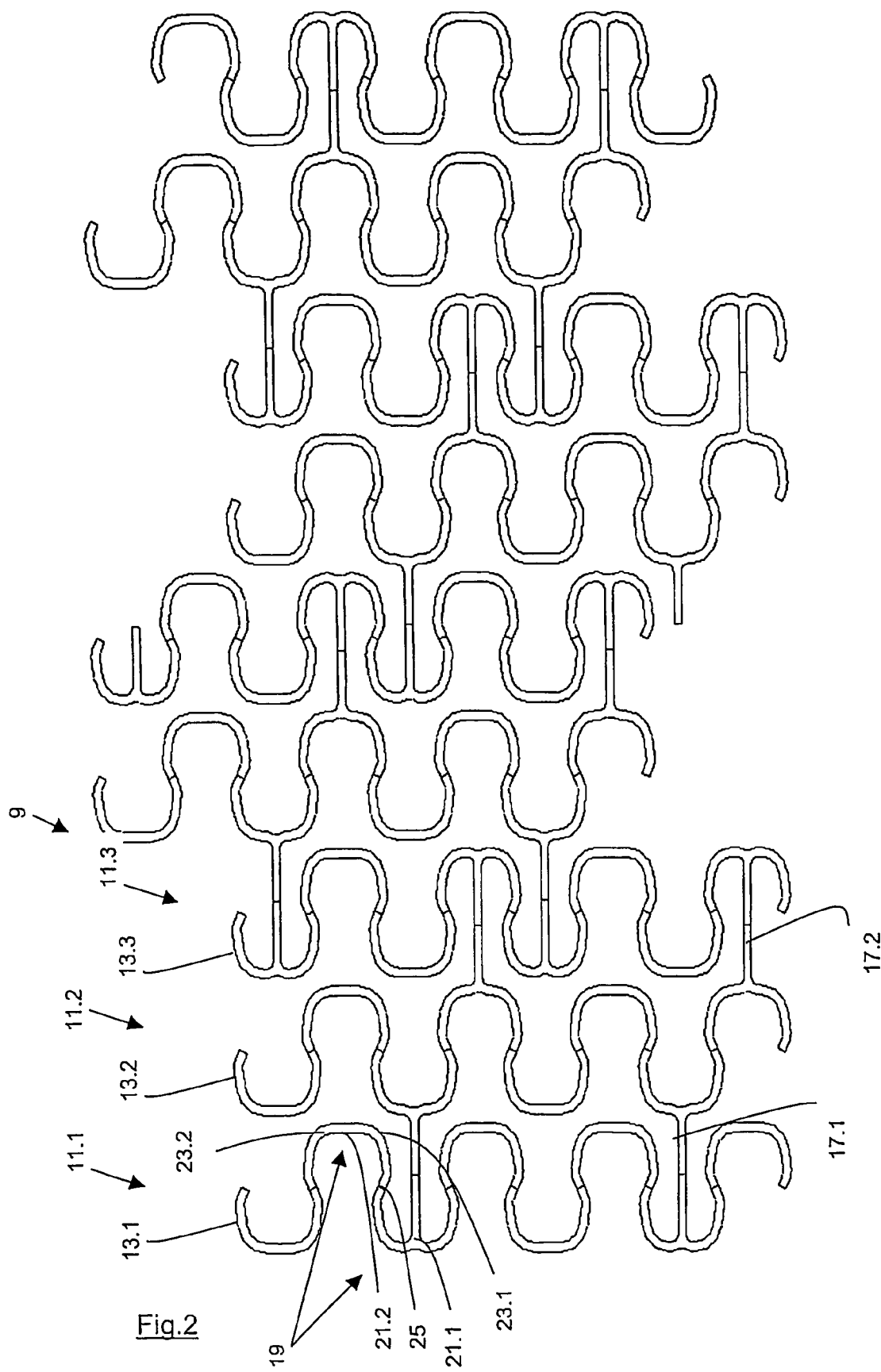
FIG. 2 is a diagrammatic section view of a stent design according to the invention according to a second varient.

FIG. 2 diagrammatically shows a section view of a further stent 9 with a multitude of structural segments 11.1, 11.2, 11.3 arranged side by side. The structural segments 11.1, 11.2, 11.3 have a loop structure comprising a brace 13.1, 13.2, 13.3 which circumferentially extends along the longitudinal axis of the stent 9. By way of transverse connectors 17.1, 17.2 the individual structural segments 11.1, 11.2, 11.3 are interconnected in longitudinal extension of the stent 9. The illustration is a top view of the windings of the circumferential wall formed by the individual support segments 11.1, 11.2, 11.3.

As far as the design options and joining options of the transverse connectors 17.1, 17.2 are concerned, reference is made to the shapes mentioned in embodiment 1.

In the turning region 19 of the loop structure, i.e. at the tips of the individual loops, the braces 13.1, 13.2. 13.3 comprise straight bending sections 21.1, 21.2, aligned in circumferential direction. The straight bending sections 21.1, 21.2 are interconnected by way of two joining points 23.1, 23.2 and a slightly double-s-shaped limb section 25. The limb section 25 of these loops is kept sufficiently short in relation to the straight sections 21.1, 21.2 so that it is almost raised when the stent 9 is expanded in circumferential direction. In this specific case the length of the straight bending section 21.2 in relation to its width is approximately 1:4, wherein the length is measured between the geometric centres of the joining points 23.1, 23.2.

Embodiment 3

Figure 3A:
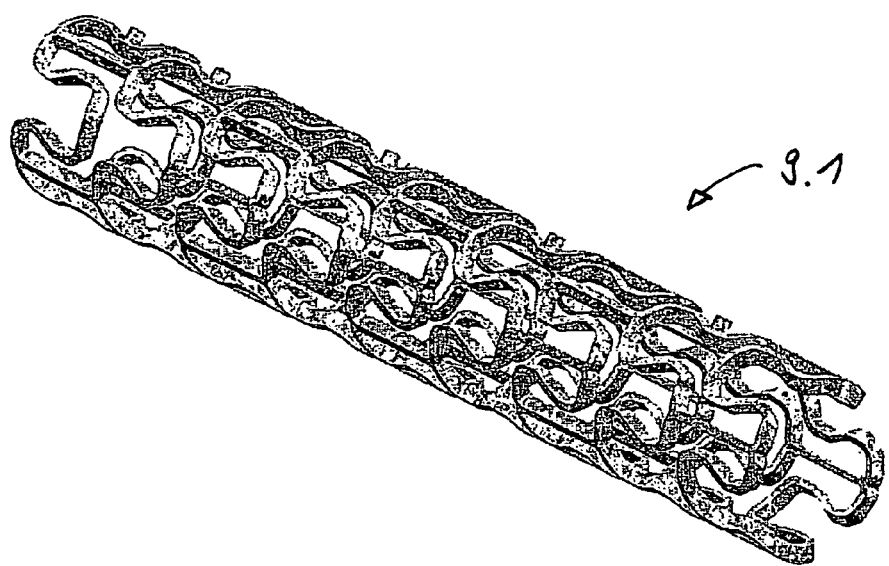
FIGS. 3a-c are a three-dimensional view of a stent with a stent design that is based on that of FIG. 2 and enlarged sections thereof.
Figure 3B:
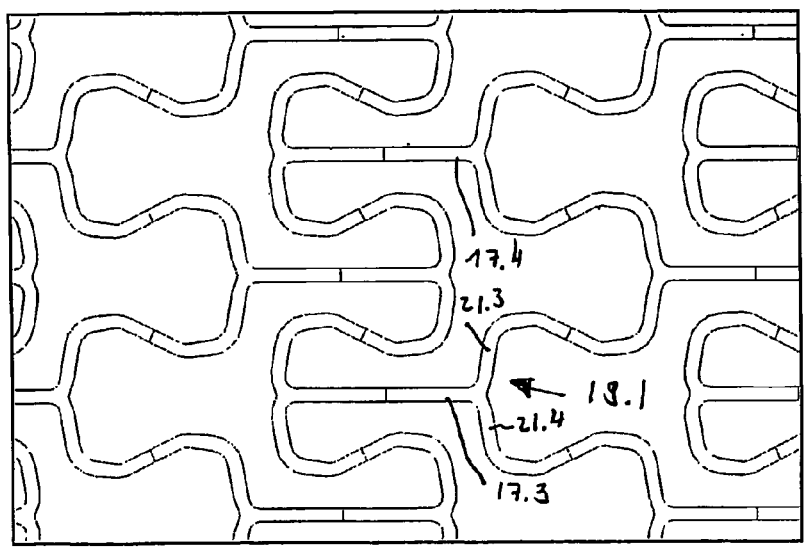
Figure 3C:
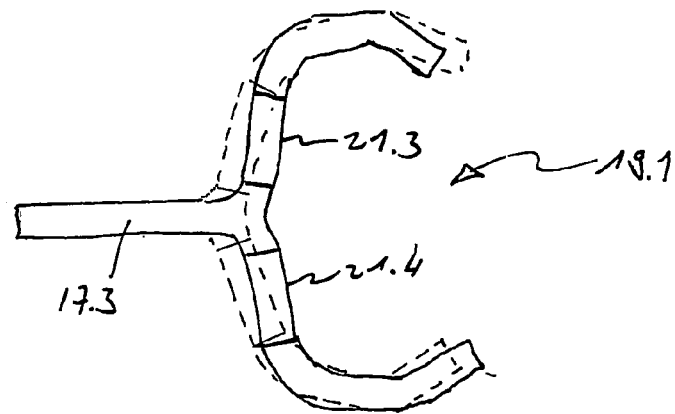

FIGS. 3a to 3c provide a three-dimensional view in enlarged sections of a stent 9.1 with a design that is almost identical to that of embodiment 2. The only difference is that in embodiment 3 transverse connectors 17.3, 17.4 now start at each turning region 19.1. The three-dimensional representation of FIG. 3a shows the stent design in the non-expanded state. As can be seen from the enlarged section of FIG. 3b, the two bending sections 21.3, 21.4 in the turning region 19.1 are not aligned exactly in circumferential direction of the stent 9.1, but instead deviate slightly, namely by approximately 8°. FIG. 3c shows an enlarged view of the turning region 19.1 with the two bending sections 21.3, 21.4 and in addition, by means of the dashed line, indicates the deformation of this region during expansion of the stent 9.1.

Embodiment 4

Figure 4A:
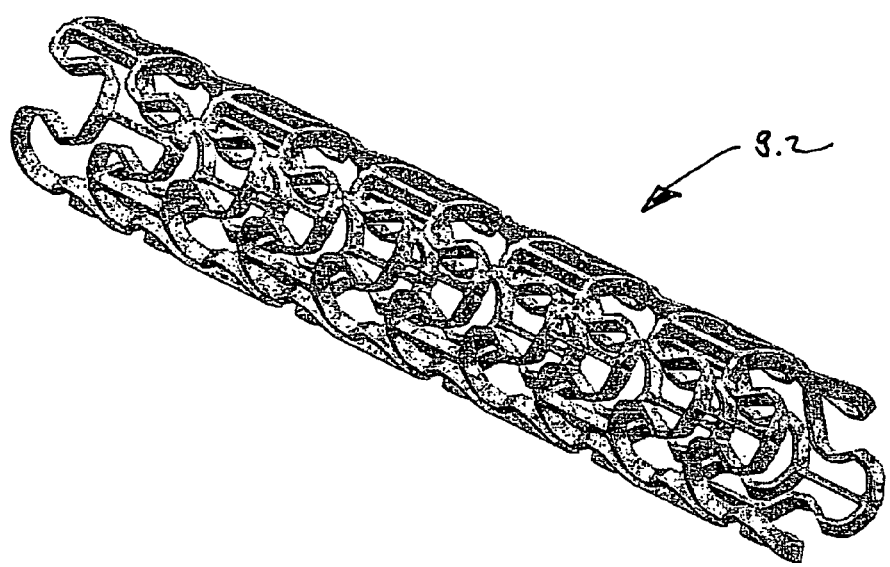
FIGS. 4a-c are a three-dimensional view of a stent with a stent design that is based on that of FIG. 2 and enlarged sections thereof.
Figure 4B:
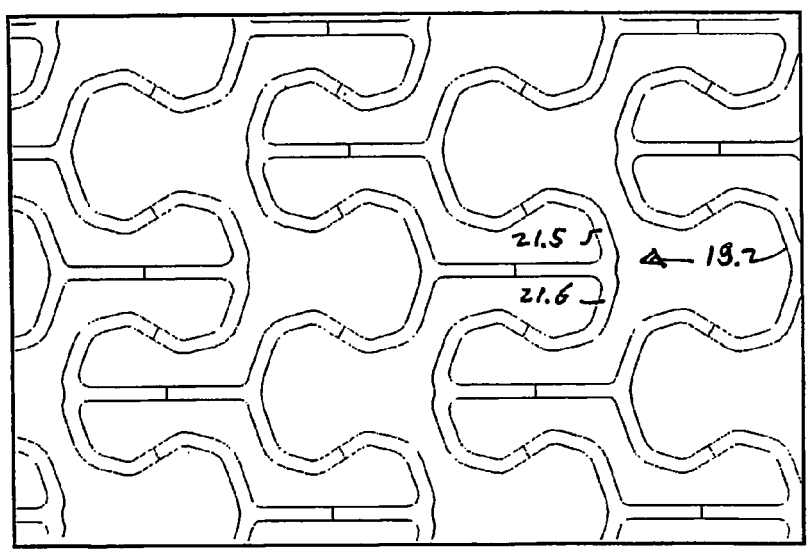
Figure 4C:
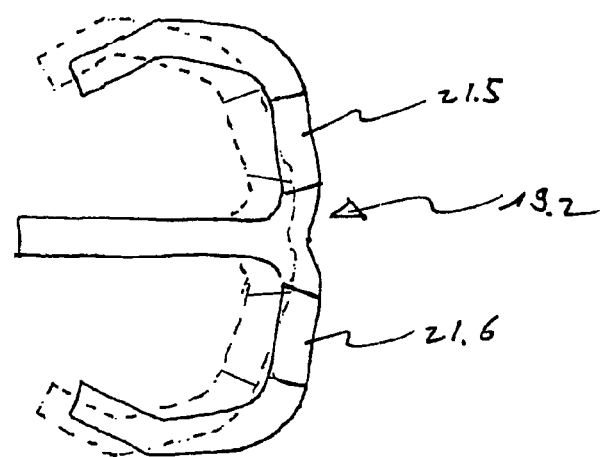

FIGS. 4a to 4c show a stent 9.2 whose design is very similar to that of embodiment 3. The differences are as follows: the two bending sections 21.5, 21.6 in the turning region 19.2 are shortened when compared to those in embodiment 3; and in the turning region 19.2 the two bending sections 21.5, 21.6 deviate somewhat more from the exact circumferential direction of the stent 9.2, namely by approximately 10° (see FIGS. 4b and 4c). FIG. 4a is a three-dimensional illustration of the stent design in the non-expanded state. FIG. 4c shows an enlarged view of the turning region 19.2 with the two bending sections 21.5, 21.6 and in addition, by means of the dashed line, indicates the deformation of this region during expansion of the stent 9.2.

Using the measures explained according to embodiments 1 to 4 a situation can be achieved in which the straight bending sections 20.1-20.3, 21.1-21.6 during expansion of the stent 9, 9.1, 9.2, 10 are predominantly subjected to a bending moment. Due to the constant lever arm or the constant moment along the entire straight bending sections 20.1-20.3, 21.1-21.6 expansion is evenly distributed and local stress concentrations and expansion concentrations are to a very large extent prevented so that account is taken of the material's short elongation at rupture.

We claim:

1. A stent comprising a material with an elongation at rupture of 30% or less and with a tubular base body which at least in part comprises structural segments which are interconnected in the longitudinal direction of the stent by way of transverse connectors and
    wherein the structural segments comprise a zigzagging or undulating structure of a brace which is wrapped around the longitudinal axis of the stent,
    wherein the brace in a turning region of the zigzagging or undulating structure comprises at least one straight bending section that extends in an essentially circumferential direction,
    wherein the brace comprises S-shaped limb sections located between the turning regions,
    wherein a first plurality of turning regions contact a transverse connector and the first plurality of turning regions comprise straight bending sections positioned on both sides of a contact point of a transverse connector, and the straight bending sections positioned on both sides of the contact point of the transverse connector are offset from a circumferential direction between about 8 and about 10 degrees and are angled in opposite directions relative to the circumferential direction, and
    wherein said S-shaped limb sections are adapted such that the limb sections extend in the circumferential direction when the stent is expanded in the circumferential direction.

2. The stent according to claim 1, wherein the ratio of length to width of the straight bending section of the brace is about 1:2 to about 1:6.

3. The stent according to claim 2, wherein the ratio is about 1:2 to about 1:3.

4. The stent according to claim 1, wherein the elongation at rupture of the material is about 5-about 30%.

5. The stent according to claim 4, wherein the elongation at rupture of the material is about 10-about 30%.

6. The stent according to claim 5, wherein the elongation at rupture of the material is about 10-about 25%.

7. The stent according to claim 6, wherein the elongation at rupture of the material is about 10-about 20%.

8. The stent according to claim 7, wherein the elongation at rupture of the material is about 10-about 15%.

9. The stent according to claim 1, wherein the stent is formed from a biodegradable metal alloy.

10. The stent according to claim 9, wherein the biodegradable metal alloy is a magnesium alloy, iron alloy or tungsten alloy.

11. The stent according to claim 1, wherein the structural segments in the longitudinal direction of the stent are arranged such that the zigzagging or undulating structures of at least two adjacent structural segments are in phase.

12. The stent according to claim 1, wherein the transverse connectors are aligned parallel to the longitudinal direction of the stent.

13. The stent according to claim 1, wherein the point of contact of the transverse connectors is situated in the middle of the straight bending sections.

14. The stent according to claim 1, wherein the transverse connectors are substantially rectilinear.

15. The stent according to claim 1, wherein said S-shaped limb sections are adapted to extend in the circumferential direction when the stent is expanded in the circumferential direction by the length of the S-shaped limb portions being kept sufficiently short in relation to the straight bending sections.

16. The stent according to claim 1, additionally comprising a second plurality of turning regions that do not contact a transverse connector.

* * * * *